United States Patent [19]
Menard

[11] Patent Number: 4,753,470
[45] Date of Patent: Jun. 28, 1988

[54] FIRST CONTACT OPHTHALMIC IMPLEMENT

[76] Inventor: France Menard, 508-1239 12 Avenue, SW, Calgary, Alberta, Canada, T3C 3R8

[21] Appl. No.: 882,427

[22] Filed: Jul. 7, 1986

[51] Int. Cl.$^4$ .............................................. A61F 9/00
[52] U.S. Cl. .................................................. 294/1.2
[58] Field of Search ................. 294/1.2, 65.5; 206/5.1; 351/160 A, 160 H

[56] References Cited

U.S. PATENT DOCUMENTS 4,037,866  7/1977  Price ........................................ 294/1.2
4,332,318  6/1982  Feldman ................................. 294/1.2

Primary Examiner—James B. Marbert

[57] ABSTRACT

This invention is a container storing a lens magnet on an end of a stem extending from a cap of the container, the magnet being made of soft silicone material.

1 Claim, 1 Drawing Sheet

U.S. Patent   Jun. 28, 1988   4,753,470
FIG.1
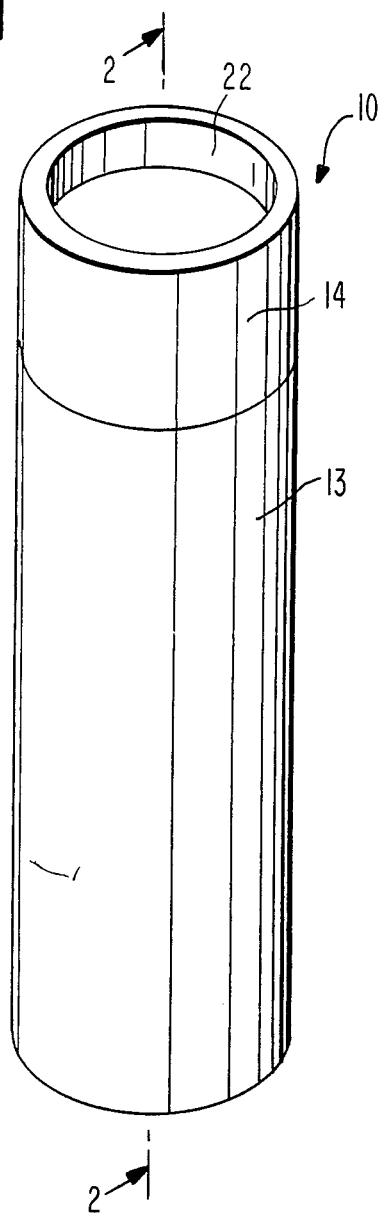
FIG. 2
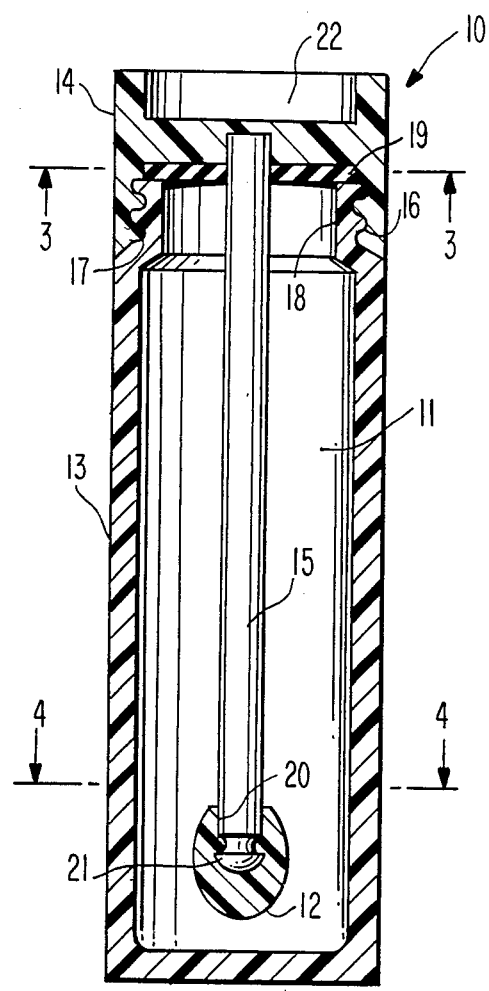
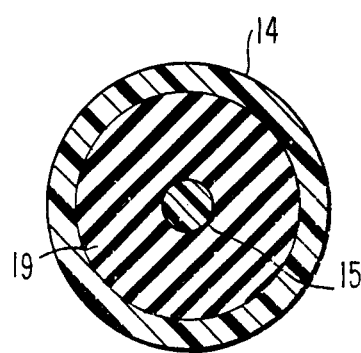
FIG.3
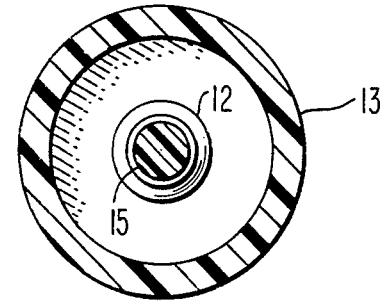
FIG.4

FIRST CONTACT OPHTHALMIC IMPLEMENT

BACKGROUND OF THE INVENTION

1. Field of the Invention

This invention relates generally to ophthalmic devices. More specifically, it relates to implements for the handling of soft contact lenses.

2. Description of Prior Art

It is well known to those persons who wear contact lenses that the most common problems associated with them is the possibility of easily tearing, ripping or abrasing them while being handled in removal from a storage case and being placed in the eye. Such damage often occurs when a person's fingernails are long and possibly also are rough or sharp. This situation is objectionable and is therefore in need of an improvement.

SUMMARY OF THE INVENTION

Therefore, it is a principal object of the present invention to provide an implement that facilitates a delicate handling of soft contact lenses so that all possibility of damage thereto is minimized or else eliminated.

Another object is to provide an ophthalmic implement which is small so as to be readily convenient for a person to carry in a pocket or purse and which accomplishes its intended task more quickly and easily.

Yet another object is to provide an ophthalmic implement that is retained in a fully hygenic condition at all times for instant use whenever needed.

Other objects are to provide an ophthalmic implement which is simple in design, inexpensive to manufacture, and is efficient in operative use.

These and other objects will be readily evident upon a study of the following Specification and the accompanying Drawing.

BRIEF DESCRIPTION OF THE DRAWINGS

FIG. 1 is a perspective view of a contact lens holder, shown in accordance with the present invention;

FIG. 2 is a cross-sectional view, taken along line 2—2 of FIG. 1;

FIG. 3 is a cross-sectional view, taken along line 3—3 of FIG. 2, and

FIG. 4 is a cross-sectional view, taken along line 4—4 of FIG. 2.

DETAILED DESCRIPTION

Referring now to the Drawing in greater detail, the reference numeral 10 represents an ophthalmic implement according to the present invention, wherein there is an enclosure 11 for storing therewithin a magnet 12 that is used for contacting a lens and holding it while being transported into the eye.

The enclosure comprises an elongated, cylindrically-shaped case 13 having a removable closure cap 14 screwed on its open end, and the cap having a long stem 15 that fits inside the case and which has the magnet attached on its end. The cap accordingly includes an internal screw thread 16 that engages an external screw thread 17 around a neck 18 of the case. A resilient seal 19 is fitted inside a bottom of the cap so as to make the enclosure leak proof for a saline solution of water that is either placed directly therewithin or else left as a coating around the magnet after the magnet has been first soaked in such solution externally and then placed therein. The lens magnet 12 is made from a specially soft silicone material, shaped to be round, and having an opening 20 for being fitted on a rounded head 21 formed on the end of the stem, so as to be readily removable and replaceable if necessary so as to be always clean.

The case and cover are molded from a hard plastic which when assembled together, measure less than three inches in overall length and being less than one inch in diameter.

A shallow well or depression 22 is formed on an outer end of the screw cap, as shown.

In use, the magnet will readily pick up a soft contact lens and transport it between a lens case and a person's eye.

While various changes may be made in the detail construction, it is understood that such changes will be within the spirit and scope of the present invention as is defined by the appended claims.

What I now claim is:

1. An ophthalmic implement comprising, an enclosure, providing storage for a contact lens, a lens magnet received in said enclosure, for adhering to said contact lens and transporting said contact lens between a lens case and a person's finger tip for further handling, a stem secured to an inner side of a cap received on said enclosure, and said lens magnet is removably received on an end of said stem and retains said contact lens by surface tension provided from a saline solution on the outer peripheral surface of said lens magnet.

* * * * *